(12) United States Patent
Burgermeister

(10) Patent No.: US 6,740,114 B2
(45) Date of Patent: May 25, 2004

(54) FLEXIBLE STENT

(75) Inventor: Robert Burgermeister, Bridgewater, NJ (US)

(73) Assignee: Cordis Corporation, Miami Lakes, FL (US)

(*) Notice: Subject to any disclaimer, the term of this patent is extended or adjusted under 35 U.S.C. 154(b) by 120 days.

(21) Appl. No.: 09/797,641

(22) Filed: Mar. 2, 2001

(65) Prior Publication Data

US 2002/0123799 A1 Sep. 5, 2002

Related U.S. Application Data

(60) Provisional application No. 60/272,696, filed on Mar. 1, 2001.

(51) Int. Cl.$^7$ .................................................. A61F 2/06
(52) U.S. Cl. .................................................. 623/1.17
(58) Field of Search ............................ 623/1.1, 1.11, 623/1.12, 1.15, 1.17

(56) References Cited

U.S. PATENT DOCUMENTS

| | | |
|---|---|---|
| 1,205,743 A | 7/1966 | Didcott |
| 3,657,744 A | 4/1972 | Ersek |
| 4,441,216 A | 4/1984 | Ionescu et al. |

(List continued on next page.)

FOREIGN PATENT DOCUMENTS

| | | |
|---|---|---|
| DE | 3205942 A1 | 9/1983 |
| EP | 0 540 290 A2 | 5/1993 |
| EP | 0 540 290 A3 | 5/1993 |
| EP | 0 734 698 A2 | 10/1996 |
| EP | 0 800 801 A1 | 10/1997 |
| EP | 0 830 853 A1 | 3/1998 |
| EP | 0 887 051 A | 12/1998 |
| EP | 1074 227 A | 2/2001 |
| FR | 566807 | 2/1924 |
| JP | 6-41745 | 6/1994 |
| WO | WO 96/26689 A1 | 9/1996 |
| WO | WO 96/34580 A1 | 11/1996 |
| WO | WO 97/25000 A1 | 7/1997 |
| WO | 9732544 * 9/1997 | ................. 623/1.15 |
| WO | WO 97/32544 A1 | 9/1997 |
| WO | WO 98/19628 A1 | 5/1998 |
| WO | WO 99/49928 A1 | 10/1999 |
| WO | WO 00/62710 A1 | 10/2000 |
| WO | WO 00/66034 A1 | 11/2000 |

OTHER PUBLICATIONS

European Search Report, dated Oct. 16, 2002, for European Appln. No. EP 02 25 1428.

*Primary Examiner*—Corrine McDermott
*Assistant Examiner*—Alvin Stewart
(74) *Attorney, Agent, or Firm*—Paul A. Coletti

(57) ABSTRACT

A preferred embodiment of a stent provides a folded strut section that provides both structural rigidity and reduction in foreshortening of the stent mechanism. A flexible section provides flexibility for delivery of the stent mechanism. In a second embodiment, flexible section columns are angled with respect to each other, and to the longitudinal axis of the stent. These relatively flexible sections are oppositely phased in order to negate any torsion along their length. In yet another embodiment, the flexible connector can take on an undulating shape (like an "N"), but such that the longitudinal axis of the connector is not parallel with the longitudinal axis of the stent. Finally, a new method is disclosed for making stents. The method consists of performing a standard photochemical machining process of cutting, cleaning and coating the tube with a photoresist. However, unlike former methods, the photoresist image is developed on the surface of the cylindrical metallic tube, which results in a controlled variable etching rate at selected sites on the cylindrical metallic tube during the etching process. Further embodiments provide living hinge connectors and connections along the length of the radial strut member.

9 Claims, 9 Drawing Sheets

U.S. PATENT DOCUMENTS

| | | |
|---|---|---|
| 4,503,569 A | 3/1985 | Dotter |
| 4,553,545 A | 11/1985 | Maass et al. |
| 4,580,568 A | 4/1986 | Gianturco |
| 4,733,665 A | 3/1988 | Palmaz |
| 4,776,337 A | 10/1988 | Palmaz |
| 4,800,882 A | 1/1989 | Gianturco |
| 4,856,516 A | 8/1989 | Hillstead |
| 4,886,062 A | 12/1989 | Wiktor |
| 4,907,336 A | 3/1990 | Gianturco |
| 4,969,458 A | 11/1990 | Wiktor |
| 4,990,131 A | 2/1991 | Dardik et al. |
| 4,990,155 A | 2/1991 | Wilkoff |
| 4,994,071 A | 2/1991 | MacGregor |
| 5,015,253 A | 5/1991 | MacGregor |
| 5,035,706 A | 7/1991 | Gianturco et al. |
| 5,041,126 A | 8/1991 | Gianturco |
| 5,064,435 A | 11/1991 | Porter |
| 5,102,417 A | 4/1992 | Palmaz |
| 5,104,404 A | 4/1992 | Wolff |
| 5,116,365 A | 5/1992 | Hillstead |
| 5,122,154 A | 6/1992 | Rhodes |
| 5,131,908 A | 7/1992 | Dardik et al. |
| 5,133,732 A | 7/1992 | Wiktor |
| 5,135,536 A | 8/1992 | Hillstead |
| 5,163,958 A | 11/1992 | Pinchuk |
| 5,171,262 A | 12/1992 | MacGregor |
| 5,176,660 A | 1/1993 | Truckai |
| 5,178,618 A | 1/1993 | Kandarpa |
| 5,192,307 A | 3/1993 | Wall |
| 5,195,984 A | 3/1993 | Schatz |
| 5,217,483 A | 6/1993 | Tower |
| 5,222,971 A | 6/1993 | Willard et al. |
| 5,246,445 A | 9/1993 | Yachia et al. |
| 5,258,021 A | 11/1993 | Duran |
| 5,266,073 A | 11/1993 | Wall |
| 5,275,622 A | 1/1994 | Lazarus et al. |
| 5,282,823 A | 2/1994 | Schwartz et al. |
| 5,282,824 A | 2/1994 | Gianturco |
| 5,290,305 A | 3/1994 | Inoue |
| 5,292,331 A | 3/1994 | Boneau |
| 5,304,200 A | 4/1994 | Spaulding |
| 5,314,444 A | 5/1994 | Gianturco |
| 5,314,472 A | 5/1994 | Fontaine |
| 5,334,301 A | 8/1994 | Heinke et al. |
| 5,342,387 A | 8/1994 | Summers |
| 5,354,257 A | 10/1994 | Roubin et al. |
| 5,354,308 A | 10/1994 | Simon et al. |
| 5,366,504 A | 11/1994 | Andersen et al. |
| 5,370,683 A | 12/1994 | Fontaine |
| 5,370,691 A | 12/1994 | Samson |
| 5,375,612 A | 12/1994 | Cottenceau et al. |
| 5,376,112 A | 12/1994 | Duran |
| 5,382,261 A | 1/1995 | Palmaz |
| 5,387,235 A | 2/1995 | Chuter |
| 5,389,106 A | 2/1995 | Tower |
| 5,395,390 A | 3/1995 | Simon et al. |
| 5,397,355 A | 3/1995 | Marin et al. |
| 5,403,341 A | 4/1995 | Solar |
| 5,405,377 A | 4/1995 | Cragg |
| 5,411,549 A | 5/1995 | Peters |
| D359,802 S | 6/1995 | Fontaine |
| 5,421,955 A | 6/1995 | Lau et al. |
| 5,423,885 A | 6/1995 | Williams |
| 5,441,515 A | 8/1995 | Khosravi et al. |
| 5,441,516 A | 8/1995 | Wang et al. |
| 5,443,477 A | 8/1995 | Marin et al. |
| 5,443,496 A | 8/1995 | Schwartz et al. |
| 5,443,498 A | 8/1995 | Fontaine |
| 5,443,500 A | 8/1995 | Sigwart |
| 5,449,372 A | 9/1995 | Schmaltz et al. |
| 5,449,373 A | 9/1995 | Pinchasik et al. |
| 5,449,382 A | 9/1995 | Dayton |
| 5,496,365 A | 3/1996 | Sgro |
| 5,527,354 A | 6/1996 | Fontaine et al. |
| 5,569,295 A | 10/1996 | Lam |
| 5,591,197 A | 1/1997 | Orth et al. |
| 5,632,763 A | 5/1997 | Glastra |
| 5,643,312 A | 7/1997 | Fischell et al. |
| 5,649,952 A | 7/1997 | Lam |
| 5,653,747 A | 8/1997 | Dereume |
| 5,669,924 A | 9/1997 | Shaknovich |
| 5,697,971 A | 12/1997 | Fischell et al. |
| 5,733,303 A | 3/1998 | Israel et al. |
| 5,755,734 A | 5/1998 | Richter et al. |
| 5,776,161 A | 7/1998 | Globerman |
| 5,800,508 A | 9/1998 | Goicoechea et al. |
| 5,807,404 A | 9/1998 | Richter |
| 5,836,964 A | 11/1998 | Richter et al. |
| 5,843,120 A | 12/1998 | Israel et al. |
| 5,861,027 A | 1/1999 | Trapp |
| 5,876,449 A | 3/1999 | Starck et al. |
| 5,913,895 A | 6/1999 | Burpee et al. |
| 5,922,020 A | 7/1999 | Klein et al. |
| 5,935,162 A | 8/1999 | Dang |
| 5,972,018 A | 10/1999 | Israel et al. |
| 6,001,123 A | 12/1999 | Lau |
| 6,017,365 A | 1/2000 | Von Oepen |
| 6,019,789 A | 2/2000 | Dinh et al. |
| 6,033,435 A | 3/2000 | Penn et al. |
| 6,059,811 A | 5/2000 | Pinchasik et al. |
| 6,090,127 A * | 7/2000 | Globerman ............... 606/194 |
| 6,123,721 A * | 9/2000 | Jang ........................ 623/1 |
| 6,129,754 A | 10/2000 | Kanesaka et al. |
| 6,171,334 B1 * | 1/2001 | Cox ....................... 623/1.15 |
| 6,179,867 B1 | 1/2001 | Cox |
| 6,190,405 B1 | 2/2001 | Culombo |
| 6,193,747 B1 | 2/2001 | Von Oepen |
| 6,203,569 B1 | 3/2001 | Wijay |
| 6,217,608 B1 | 4/2001 | Penn et al. |
| 6,231,598 B1 * | 5/2001 | Berry et al. ............. 623/1.15 |
| 6,293,967 B1 | 9/2001 | Shanley |
| 6,309,414 B1 * | 10/2001 | Rolando et al. ......... 623/1.15 |
| 6,325,821 B1 | 12/2001 | Gaschino |
| 6,340,366 B2 | 1/2002 | Wijay |
| 6,344,055 B1 | 2/2002 | Shukov |

\* cited by examiner

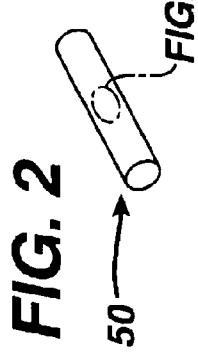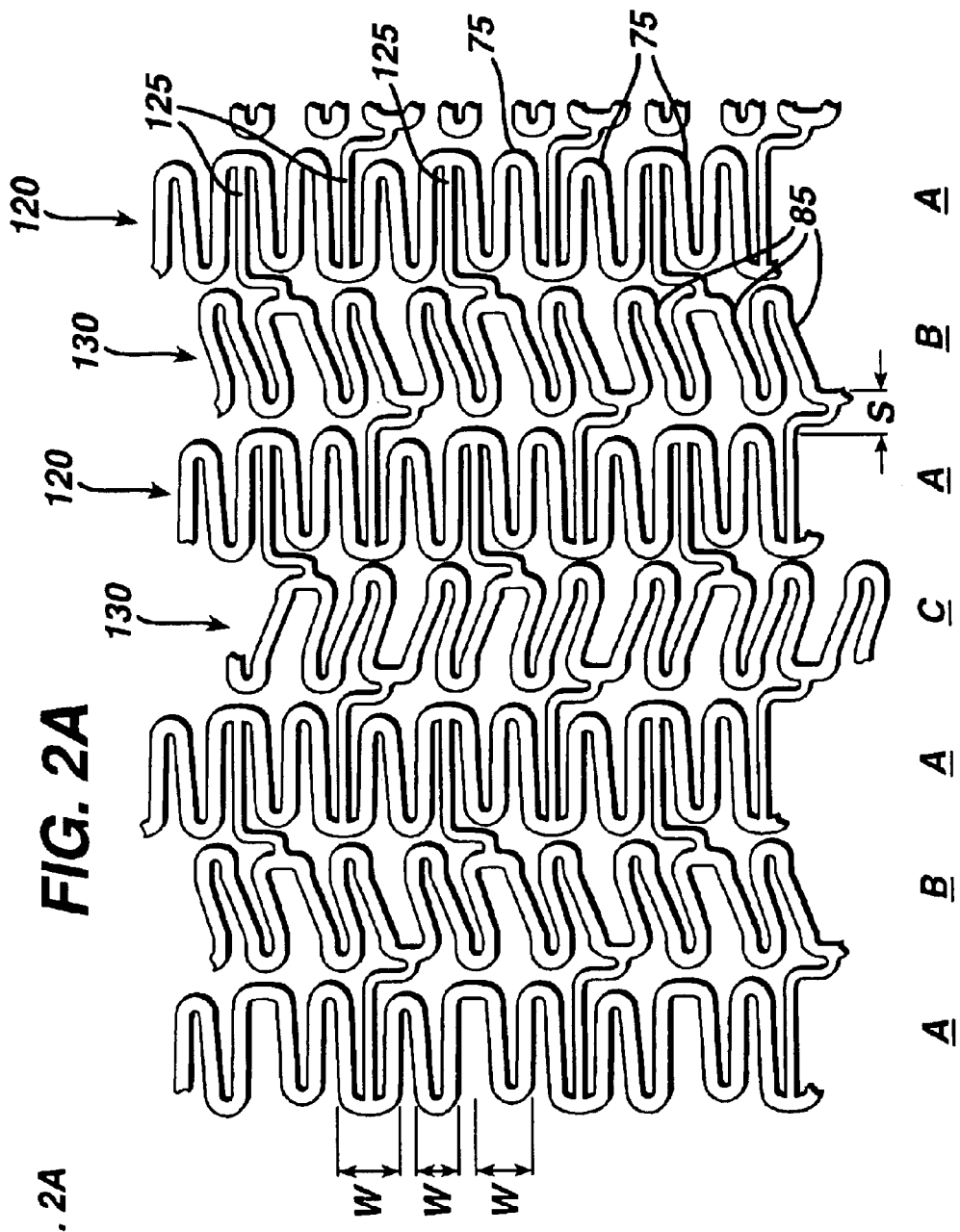
FIG. 2
FIG. 2A

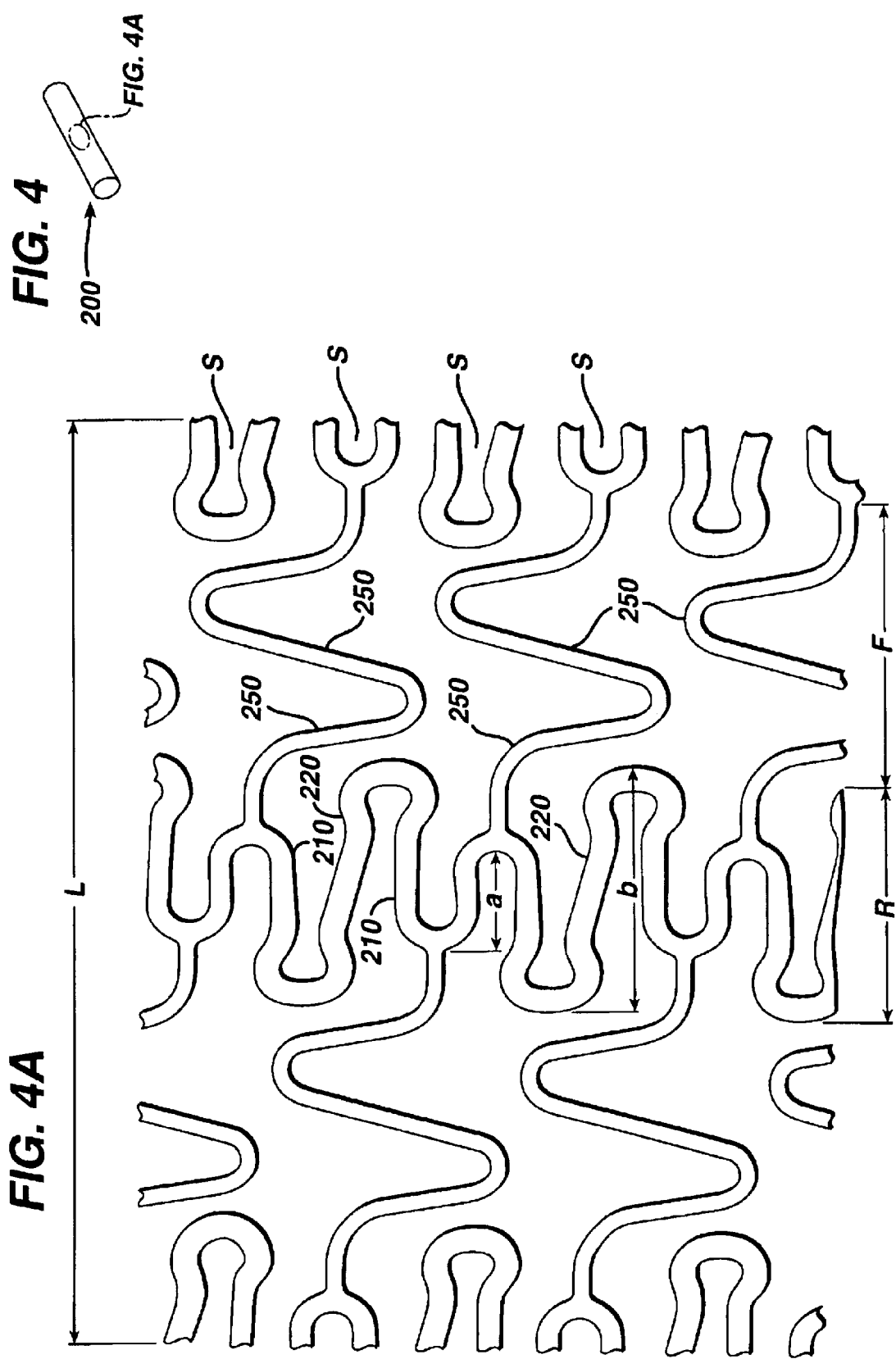

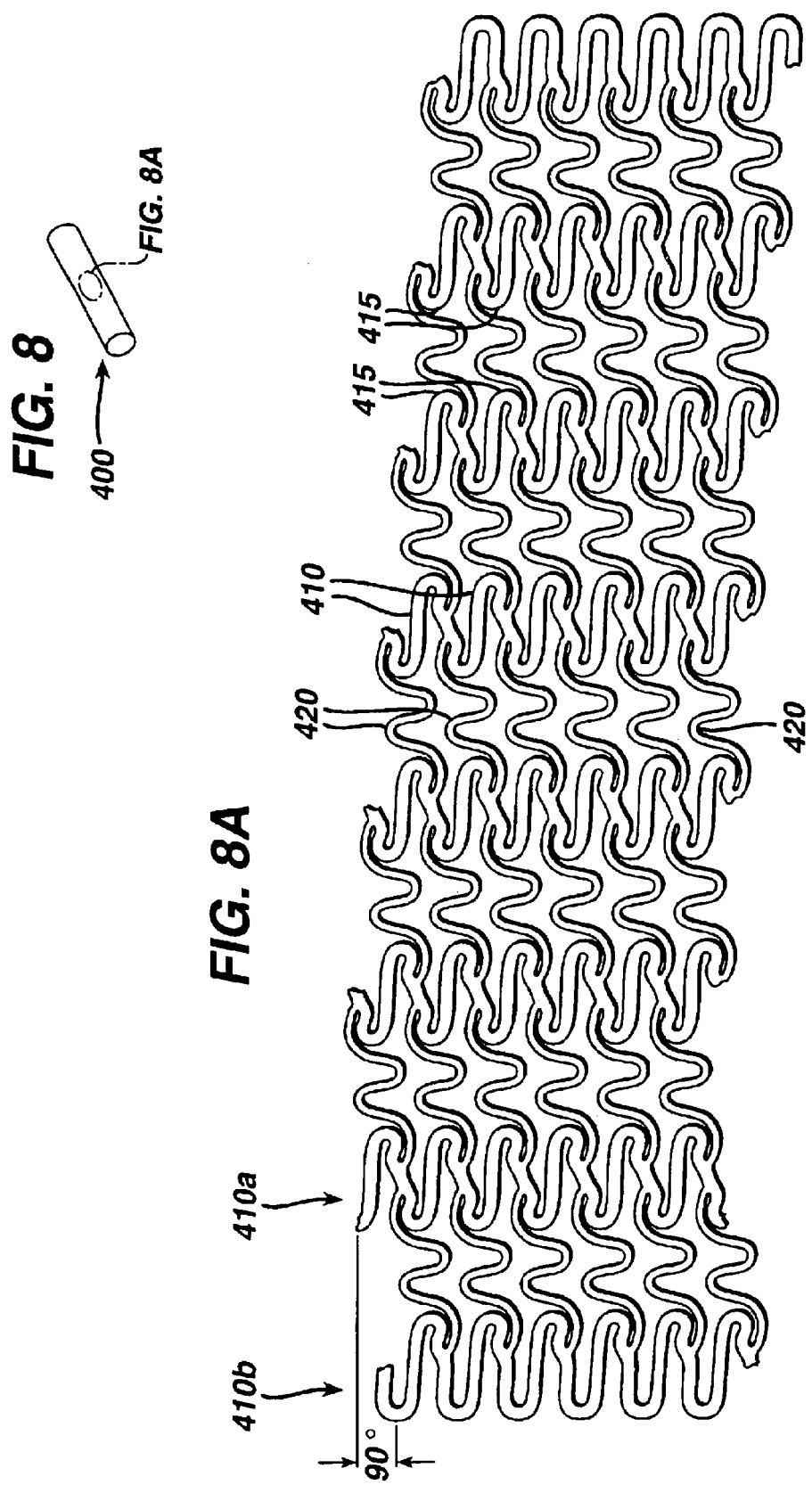

FLEXIBLE STENT

This Application claims the benefit to U.S. provisional application Ser. No. 60/272,696 filed Mar. 1, 2001.

BACKGROUND ART

A stent is commonly used as a tubular structure left inside the lumen of a duct to relieve an obstruction. Commonly, stents are inserted into the lumen in a non-expanded form and are then expanded autonomously (or with the aid of a second device) in situ. A typical method of expansion occurs through the use of a catheter mounted angioplasty balloon, which is inflated within the stenosed vessel or body passageway, in order to shear and disrupt the obstructions associated with the wall components of the vessel and to obtain an enlarged lumen.

In the absence of a stent, restenosis may occur as a result of elastic recoil of the stenotic lesion. Although a number of stent designs have been reported, these designs have suffered from a number of limitations. These include restrictions on the dimension of the stent.

Other stents are described as longitudinally flexible but consist of a plurality of cylindrical elements connected together. This design has at least one important disadvantage, for example, according to this design, protruding edges occur when the stent is flexed around a curve raising the possibility of inadvertent retention of the stent on plaque deposited on arterial walls. This may cause the stent to form emboli or move out of position and further cause damage to the interior lining of healthy vessels.

Thus, stents are known in the art. Such stents may be expanded during or just after balloon angioplasty. As a general rule, the manufacture of a stent will need to compromise axial flexibility in order to permit expansion and provide overall structural integrity.

Prior stents have had a first end and a second end with an intermediate section between the two ends. The stent further has a longitudinal axis and comprises a plurality of longitudinally disposed bands, wherein each band defines a generally continuous wave along a line segment parallel to the longitudinal axis. A plurality of links maintains the bands in a tubular structure. In a further embodiment of the invention, each longitudinally disposed band of the stent is connected, at a plurality of periodic locations, by a short circumferential link to an adjacent band. The wave associated with each of the bands has approximately the same fundamental spatial frequency in the intermediate section, and the bands are so disposed that the waves associated with them are spatially aligned so as to be generally in phase with one another. The spatial aligned bands are connected, at a plurality of periodic locations, by a short circumferential link to an adjacent band.

In particular, at each one of a first group of common axial positions, there is a circumferential link between each of a first set of adjacent pairs of bands.

At each one of a second group of common axial positions, there is a circumferential link between each of a second set of adjacent rows of bands, wherein, along the longitudinal axis, a common axial position occurs alternately in the first group and in the second group, and the first and second sets are selected so that a given band is linked to a neighboring band at only one of the first and second groups of common axial positions.

Furthermore, this stent can be modified to provide for bifurcated access, whereas the stent itself is uniform throughout. If the manufacturer designs such a stent to have an large enough opening, then it is possible to place the stent such that a pair of stents can be placed one through the other. In this fashion, the stents are capable of being placed at a bifurcation, without any welding or any special attachments. An interlocking mechanism can be incorporated into the stent design to cause the stent to interlock at the desired position during assembly of the device.

Further, a metallic stent has been designed which contains a repeating closed loop feature. The stent is designed such that the closed loop does not change dimensions during expansion. The composite stent is created by filling the area enclosed by the loops with a material that enhances clinical performance of the stent. The material may be a ceramic or a polymer, and may be permanent or absorbable, porous or nonporous and may contain one or more of the following: a therapeutic agent, a radio-opaque dye, a radioactive material, or a material capable of releasing a therapeutic agent, such as rapamycin, cladribine, heparin, nitrous oxide or any other know drugs, either alone or in combination.

It has been seen, however, that it may be desirable to provide for stents that have both flexibility to navigate a tortuous lesion as well as increased column strength to maintain the rigidity necessary after emplacement into the lumen of the body. The preferred designs tend to provide the flexibility via undulating longitudinal connectors. The rigidity is generally provided via the mechanism of slotted tubular stents. It is perceived that there may be mechanisms capable of enhancing the characteristics of these types of stents. Such a stent would be both flexible in delivery and rigid upon emplacement.

Furthermore, it is desirable to be able to produce stents in which the cross-sectional profile of either the struts or the connecting members is tapered (or variable) in size. In addition, it may be desirable to modify stents to have non-rectangular cross-sections. In both these cases, different manufacturing methods may aid in the creation of such stents.

SUMMARY OF THE INVENTION

It is an object of the invention to provide a stent having has relatively little foreshortening.

It is an object of the invention to provide a stent having an enhanced degree of flexibility.

It is an object of the invention to provide such a stent while diminishing any compromise in the stent's structural rigidity upon expansion.

It is a further object of the invention to provide a novel method for manufacturing stents.

These and other objects of the invention are described in the following specification. As described herein, a preferred embodiment of a stent provides for a device that contains a flexible section and a folded strut section. The folded strut section opens (like a flower) upon expansion. This folded strut section provides both structural rigidity and reduction in foreshortening of the stent mechanism. The flexible section provides flexibility for delivery of the stent mechanism.

In a second embodiment of the device, there is a columnar section and a flexible section. The columnar section provides for a device that lengthens in the longitudinal direction upon expansion. The flexible section provides for a section that shortens somewhat in the longitudinal direction upon expansion. As a result, there is no shortening or lengthening of the stent during expansion. The flexible section columns are angled, one with respect to the other, and also with respect to the longitudinal axis of the stent, in order to provide flexibility during delivery. This arrangement also to also provide additional resistance to the balloon to prevent "dog-boning" of the stent on the balloon during delivery and slippage of the balloon along the stent. These relatively flexible sections are oppositely phased with respect to one another in order to negate any torsion along their length. These flexible sections can further be crimped onto the balloon catheter with a generally smaller profile than prior stent, so that the retention of the stent on the balloon is increased.

In yet another embodiment of the stent of the present invention, the flexible connector can take on an undulating shape (like an "N"), but such that the longitudinal axis of the connector is not parallel with the longitudinal axis of the stent. In this fashion, the flexibility is controlled in a pre-selected axis, which is not the longitudinal axis of the stent. Such an arrangement may be desired, for instance, when one chooses to place a stent in a particularly configured vasculature that has been predetermined by known means, such as intravascular ultrasound ("IVUS.")

In still a further embodiment of the present invention, there are provided "living hinge" connectors, which connect the generally flexible connectors to the stronger radial strut members. These living hinges accomplish a number of the same characteristics found in the prior embodiments disclosed herein. First, because the living hinges tend to expand upon inflation, foreshortening of the length of the stent is further reduced. Second, there is a combined radial strength provided at the intersection between the living hinges and the radial strut members. This creates a small "hoop," which is further resistant to kinking or collapse in situ. Third, as a corollary to the second attribute described above, the living hinge connectors provide for reduced strain along an equivalent length of stent.

In yet another preferred embodiment of the stent of the present invention, the connection point between the radial members and the connector members is moved to a position along the length of a radial strut. Typically, the connection may be placed at a position somewhere midway along the length of the strut. By moving the connection point of the flex connectors closer to the midpoint of the radial ring one can address foreshortening in an controlled fashion. In fact, balloon interaction aside, the connector does not have to stretch to compensate for foreshortening. When the flex connectors are connected at the midpoint of the radial ring, the distance/length through the middle portion of the stent between radial rings will remain unchanged. This is because the midpoint stays relativiely in the same position while the radial arcs of each strut move closer to the midpoint from both sides. By moving the location of the flex connector attachment beyond the mid-point of a strut, to the opposing side, one can actually capitilize on the strut moving closer to the midpoint and thus lengthen the stent upon expansion.

In addition, in the present embodiment described, adjacent radially rings start out of phase in the unexpanded state. Due to the diagonal oreintation of the connection points of the flexible connectors, upon expansion the radial rings tend to align themselves ("in" phase.) This results in more uniform cell space and thus improved scaffolding of the vessel. Further, there is described a "wavy" strut configuration, thereby facilitating both a reduced crimp profile for attaching the flexible connectors at or near a strut mid-point and reduced strain upon expansion, due to the strut itself contributing to a portion of the expansion.

Finally, a new method is disclosed for making stents. In this method there is novel photochemical machining of a cylindrical tube. The method consists of performing a standard photochemical machining process of cutting, cleaning and coating the tube with a photoresist. However, unlike former methods, the photoresist image is developed on the surface of the cylindrical metallic tube, which results in a controlled variable etching rate at selected sites on the cylindrical metallic tube during the etching process. The photoresist image consists of a series of circular regions of photoresist of varying diameters configured at varying distances along the stent. As the diameter of the circular photoresist pattern decreases and the distance between the circular photoresist patterns along the stent increases, the etch rate of the device increases. The photoresist pattern variation results in a variation in the metal removed during the etching process.

This process can be used to locally change the geometry of the cylindrical metallic tube. An advantage seen by this process is the ability to manufacture a tapered strut along the stent. Further, struts of cylindrical or other non-rectangular cross-section can be manufactured. In addition, surface contours can be placed on the stent, for instance, to allow for a reservoir to be placed in the stent to deliver drugs.

These and further objects of the invention will be seen from the following drawings and Detailed Description of the Invention.

DETAILED DESCRIPTION OF THE DRAWINGS

FIGS. 2 and 3 are plan views of an alternative embodiment of a stent of the invention;

FIG. 4 is a plan view of yet another embodiment of a stent of the invention;

FIG. 8 is a plan view of a further alternate embodiment of the present invention.

DETAILED DESCRIPTION OF THE INVENTION

Figure 1:
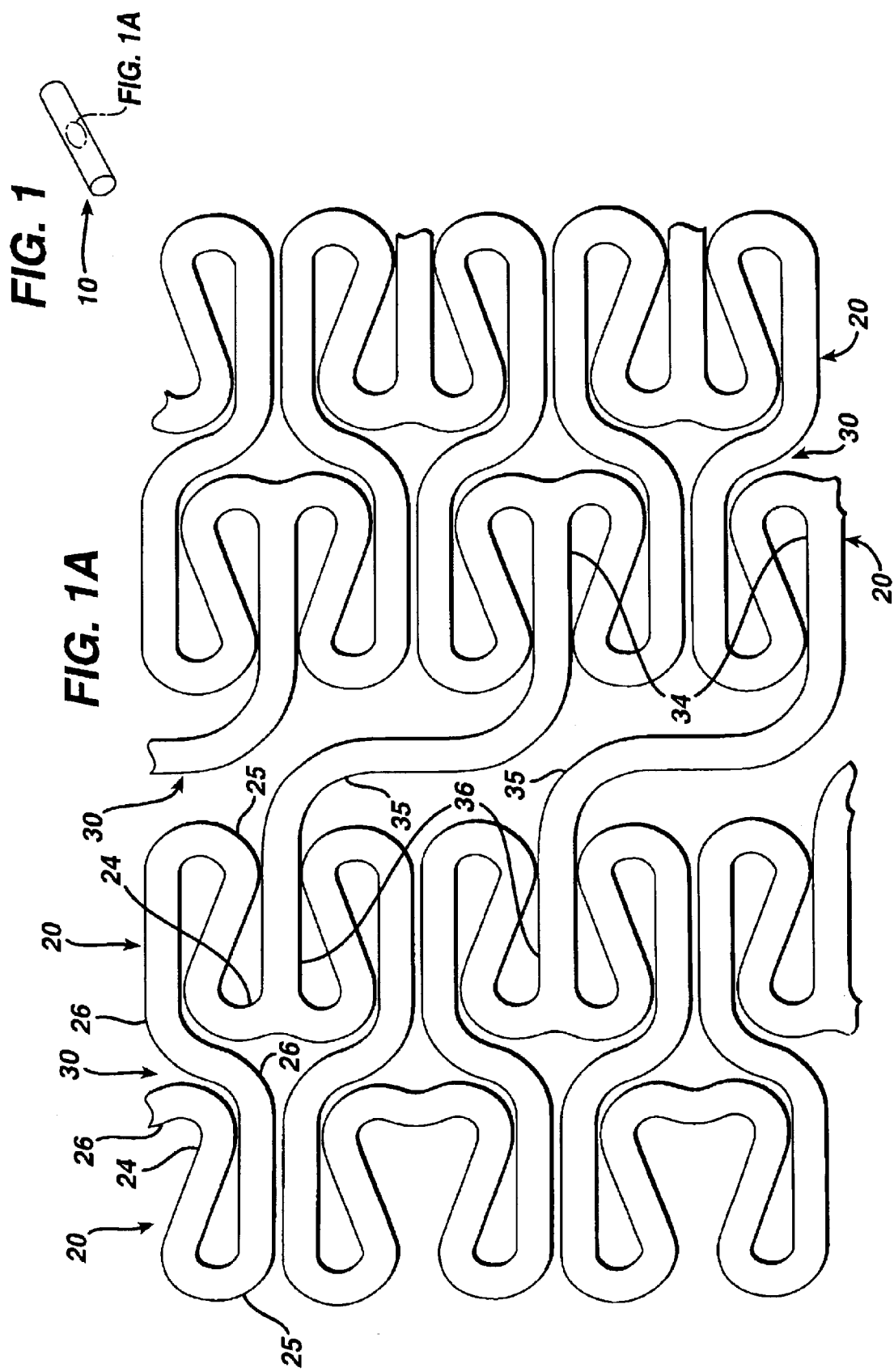
FIG. 1 is a plan view of a stent embodying the invention.
Figure 3:
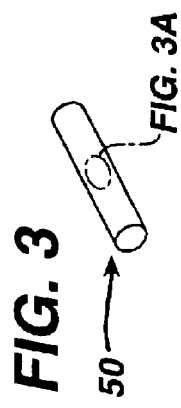
Figure 3A:
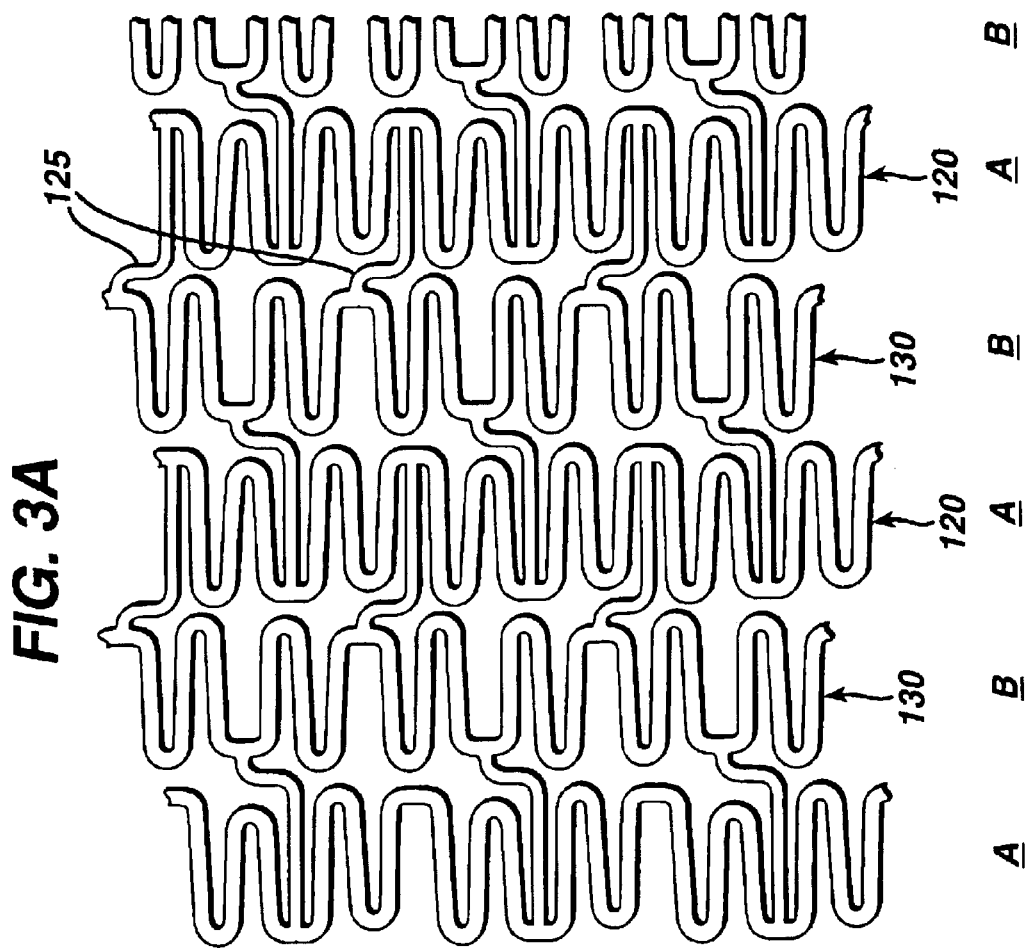

As can be seen in FIG. 1, there is described a cylindrical stent 10 which has a series of folded strut sections 20 connected by a series of flexible sections 30. The folded strut sections 20 comprise a generally folded strut member 25 having a pair of ends 24, 26. Each of the pair of ends 24, 26 is connected to another folded strut member 25 and also to the end of a flexible member 35. Thus, each end 34, 36 of a flexible member 35 is connected to two ends 24, 26 of a folded strut 25 section member.

Each of the folded struts 25 takes on a generally irregular pattern. On the other hand, each of the flexible sections 35 takes on a generally undulating pattern. The folded strut sections 20 wrap circumferentially around the cylindrical shape of the stent 10. Each flexible section 30 also connects to a folded strut section 20 around the circumference of the stent. It will be noticed that each adjacent flexible section 30 is positioned 180° out of phase with each other.

The longitudinal lengths of the folded struts 20 are short enough to give a smooth profile when the stent is bent. The folded strut 20 allows for a large diametrical expansion range upon expansion. So, upon expansion, the folded struts 20 expand circumferentially and become hoop-like so that maximum radial strength is achieved. The flexible members 30 placed between the folded struts improve the stent deliverability in the unexpanded dimension of the stent 10. These flexible members are longitudinally compliant so that foreshortening is minimized upon expansion.

In use, therefore, the stent 10 of the present invention is placed on a balloon catheter and is snaked through the vasculature to be placed into a lesion site in an artery, typically a coronary artery. Because the flexible sections 30 are so substantially flexible, they are able to navigate tortuous lesions with relative ease. Once in place, the balloon catheter is expanded by conventional means. Upon expansion, the struts 25 in the folded strut sections 20 expand to obtain a hoop-like shape. In addition, these members expand longitudinally, so that any reduction in foreshortening is negated. Of course, upon expansion, the flexible members 35 straighten so that there is further strength achieved by the stent in the straightened and rigid positions.

A variation of the present invention can be seen in the stent 50 of FIGS. 2 ("angled" version) and 3 ("straight" version). There, the radial strength sections 120 are achieved with generally straight members 115, although these members do not have folded struts. Connection between generally straight members 115 is made by connecting the generally straight members 115 to the more flexible members 125, much like the connection made involving the connecting members of the first embodiment of FIG. 1.

The members that reduce foreshortening are angled members 130 which are seen to be 180° out of phase with one another. The connection between the flexible members is made at the end of a particular relatively non-flexible member and at the distal end of a particular angled canted member 130. Now, when the columns comprised of relatively rigid members 115 expand, the length of these members 130 shorten. But, the longitudinal lengths of the canted members 130 are placed at an angle compared to the longitudinal axis of the stent 50. So, upon expansion, these canted members 130 actually lengthen with respect to the longitudinal axis of the stent 50. The net result is that no foreshortening occurs upon expansion of stent 50.

The canted members 130 are angled in order to both: increase flexibility; and to provide additional resistance on the balloon surface. This arrangement helps prevent what is known as "dogboning" or exposure of leading edge of any of the strut members 75 contained at either end of the stent 50. In addition, this configuration also prevents slippage of the stent along the balloon surface. The canted members 130 are canted in opposite phase (i.e., with a phase change of 180°) to one another, in order to negate any torsional effects on the struts 75, 85 along the length of the stent. These particular members can be crimped to a lower profile than the more rigid members, in order to ensure increased retention of the stent on the surface of a balloon catheter. Further the configuration described herein has a uniquely folded configuration reducing any risk of "flaring" of the edges of struts 75, 85 during traversal of the lumen.

It is to be noticed that the longitudinal position (the "order") of the columns can be changed if one desires a smaller initial profile. That is, if one desires that the profile be smaller, it is possible to remove the more rigid sections 120 (or a portion thereof,) and replace them with the generally canted sections 130.

It is also to be noticed that the wave amplitudes of the struts in a particular column are not kept constant. The wave amplitudes, defined herein as "W," can be lengthened where permitted by the geometry. For instance, notice the space S created between one set of strut members A and a second set of strut members B. This particular configuration allows an increased expansion range around the unexpanded circumference of the stent, while maintaining an appropriate expansion area associated with the metallic struts placed around of the circumference of the stent. Such optimization of the strut surface area is important to ensure adequate coverage of the lesion upon expansion of the stent.

The stent 50 of this particular embodiment is expanded in much the same way as the stent 10 of FIG. 1. When expansion occurs via the balloon catheter, the canted members 130 tend to lengthen and prevent foreshortening of the stent 50; the relatively rigid members 120 tend to shorten in the longitudinal direction, but in so doing provide a greater rigidity for the fully expanded stent. It is to be understood however, that in the expansion of both stents 10, 50 the ability to flexibly navigate the vasculature is enhanced from configuration of either stent 10, 50, as the case may be. All the while, the likelihood of stent foreshortening upon expansion is greatly reduced.

As can be seen in FIG. 4, one can also provide for a stent 175 that does not contain canted sections. Yet, the stent 175 expands with decreased foreshortening along its length due to the unique geometry of the stent 175. Here, the stent struts 180, 190 provide for a relatively constant length along the longitudinal axis. (In other words, the longitudinal dimension of the struts 180, 190 in combination remains relatively constant, whether in the expanded or unexpanded condition.) In this fashion, upon expansion, the stent 175 maintains a generally constant length in any of its expanded, unexpanded or partially expanded conditions.

Figure 5:
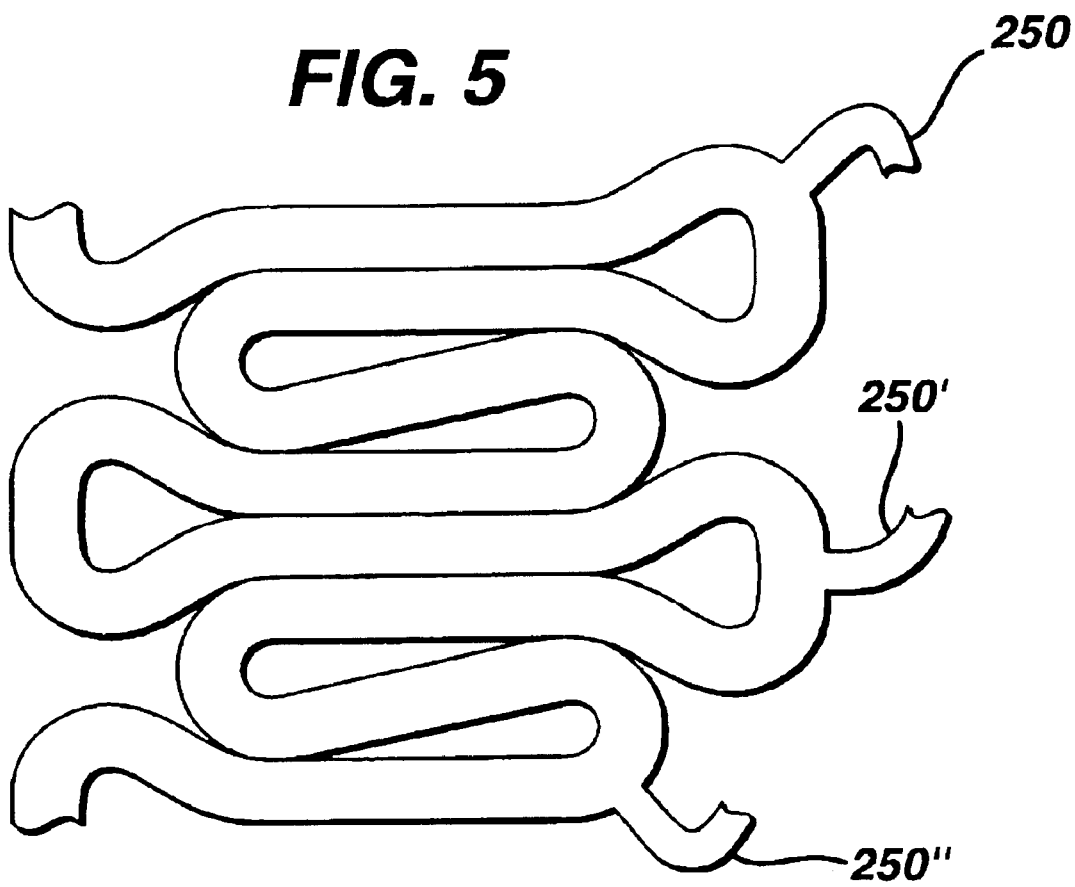
FIG. 5 is a close up of the identified section of FIG. 4 taken along lines b—b of FIG. 4.

FIGS. 4 and 5 show yet another embodiment of the design of a similar stent 200. Here, the connector 250 is shaped like an "N," much after the same fashion of "N"-shaped connectors found commercially in the Bx Velocity® stent sold by Cordis Corporation, Miami Lakes Fla. and which is at least somewhat characterized in Ser. No. 09/192,101, filed Nov. 13, 2000, now U.S. Pat. No. 6,190,403 B1, and Ser. No. 09/636,071, filed Aug. 10, 2000, both of which are assigned to Cordis Corporation, and incorporated herein by reference.

In the stent 200, the relatively rigid sections R contain unequal struts 210, 220 of lengths a, b, as can best be seen in FIG. 4. Moreover, as can be seen in FIG. 5, this strut pattern is formed so that the attachment points a at the end of the flexible connectors 250 can be located at any point along the struts 210, 220 rigid section. In this fashion, when the stent is expanded, the relatively more rigid section R "holds" the connector 250 along the surface of the lesion, so that tenacity of the stent, and its concomitant support are both maintained to a high degree at the situs of the lesion. Yet, in the unexpanded configuration, the "N"-shaped flexible connectors 250 are able to guide the stent 200 around the curvature of generally any tortuous vessel, including tortuous coronary arteries.

As can be seen from FIGS. 4 and 5, the alternative embodiment stent 200 is also capable of reducing foreshortening along its entire length. This stent contains relatively rigid sections R and relatively flexible sections F containing connectors 250. (The flexible sections F are in the form of undulating longitudinal connectors 250.) The relatively rigid sections R generally contain a slotted form, created with struts 210, 220 around a slot S. The relatively rigid sections R contain these interlaced struts 210, 220, which are of varying longitudinal dimensional length.

As can be seen from the figures, in some radial positions, the struts 210 are made longer. In other radial positions, the struts 220 are made shorter. However, the shorter struts 220 are of a constant length b in the longitudinal dimension, and in the fashion in which they connect to the relatively flexible connectors 250. Also, as described above, the relatively more rigid sections R maintain the relatively more flexible sections F at a generally constant longitudinal length due to the friction maintained by the relatively more rigid sections R on a balloon portion of an angioplasty type balloon catheter. Accordingly, upon expansion, the constant length b, in conjunction with the generally constant length of the relatively flexible connector 250, causes the stent 200 to maintain a relatively constant longitudinal dimension L in any diameter to which it is expanded. As can be appreciated, the maintenance of a constant length is desirable from the perspective of secure, repeatable placement of the stent within the vasculature.

Continuing to describe the stent 200 of FIGS. 4 and 5, the flexible sections F operate with the behavior of the flexible connectors 250 acting in the fashion of "N"-shaped flexible connectors of similar type. That is, the flexibility of the stent 200 is focused in this area F so that one is able to traverse tighter lesions using such a configuration. The relatively stronger sections R are capable of expansion to a stronger plastically deformed dimension, so that in this fashion the stent 200 is capable of supporting the arterial wall. Even though the longitudinal dimensions of the struts 210, 220 in the relatively stronger sections R are of unequal length, such a configuration does not diminish radial support in the expanded condition. Accordingly, it can be appreciated that a stent of this shape will adequately support the arterial walls at the lesion site, while maintaining radial flexibility, and longitudinal length.

Figure 7:
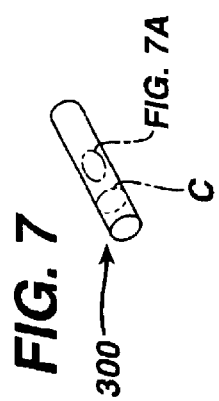
FIG. 7 is a plan view of yet another alternate embodiment of the present invention.
Figure 7A:
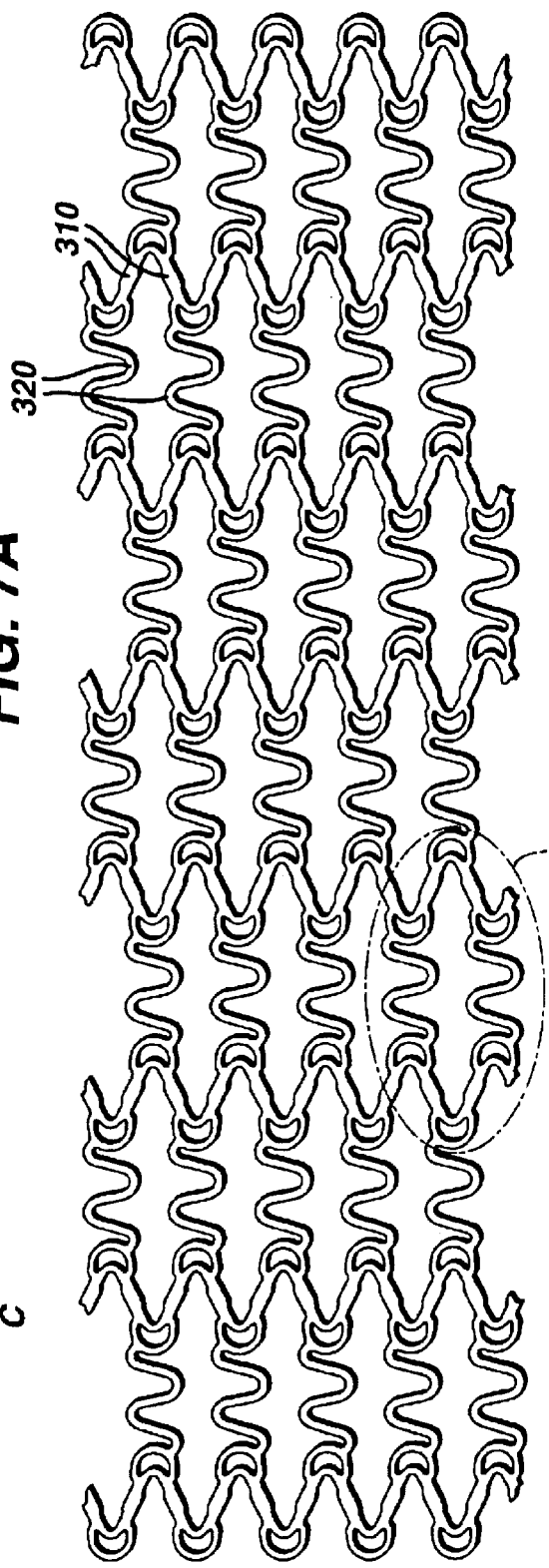
Figure 7B:
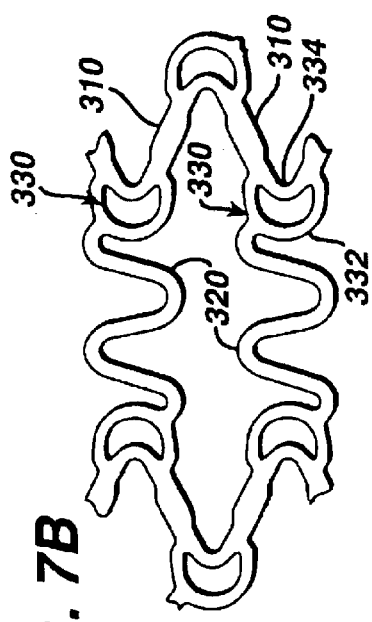

As can be best seen in FIG. 7, yet another alternate embodiment of the present invention is described. In FIG. 7, there is contained a stent 300 much like the Bx Velocity® stent sold by Cordis Corporation, Miami Lakes, Fla. In FIG. 7 there is contained on the stent 300 generally flexible connector members 310 connected to generally rigid radial strut members 320. The connector members 320 are generally formed in the shape of the letter "N", and the struts 310 are generally slots formed in a radial fashion around the circumference of the stent. The connection made between the flexible connectors 320 and the radial strut members 310 is formed from a living hinge 330. This living hinge 330 contains outer radial arc 332 and an inner radial arc 334. In the expanded configuration, the radial arcs 332, 334 move away one from the other, so that the overall length of the living hinge 330 actually increases upon expansion.

Known conventional means, such as angioplasty balloons, or the balloon on a stent delivery system expands the stent 300 of the present invention. Upon expansion, there are provided a number of benefits by the stent 300 of the present invention. First, as explained above, there is reduced foreshortening of the stent 300, since the outer radial arc 332 in fact does not foreshorten. Since it lengthens slightly, the overall length of the stent 300 is maintained to its general nominal length. There is also provided increased radial strength since the radial arcs 332, 334 at their connection between the flexible and radial struts 320, 310, (both inner and outer radial arcs 334, 332) combine to give superior strength in the arcs' section; the radial strut 310 provides for optimal strength in the radial direction since it is parallel to the loading direction of the stent 300, thereby creating a "hoop" a circumference C of the stent. Also, because the radial arcs are able to accept greater forces, there is reduced strain for the equivalent strength designed for a stents. In all, the stent 300 of this embodiment provides for at least equivalent radial strength, less foreshortening and reduced strain when compared to current stents.

Figure 9:
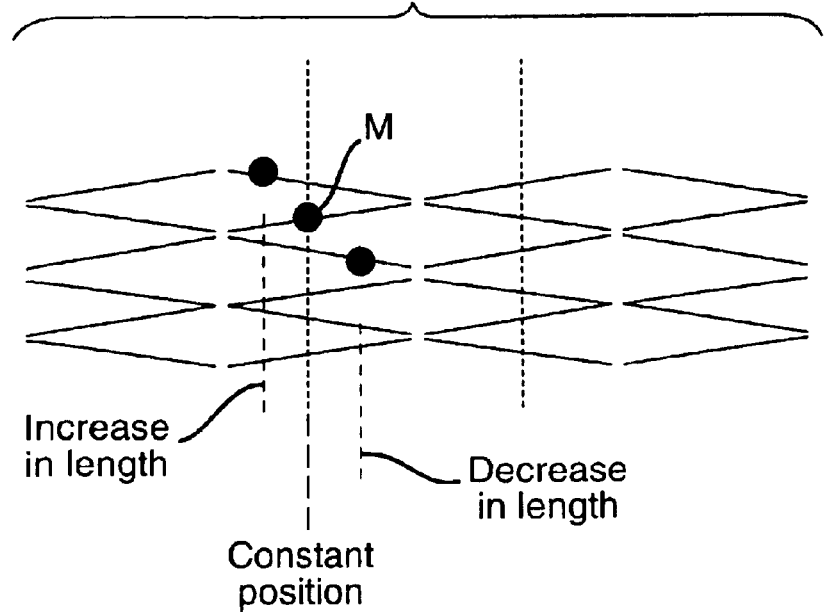
FIGS. 9 and 10 are schematics of the theory behind expansion of the stent of FIG. 8.
Figure 10:
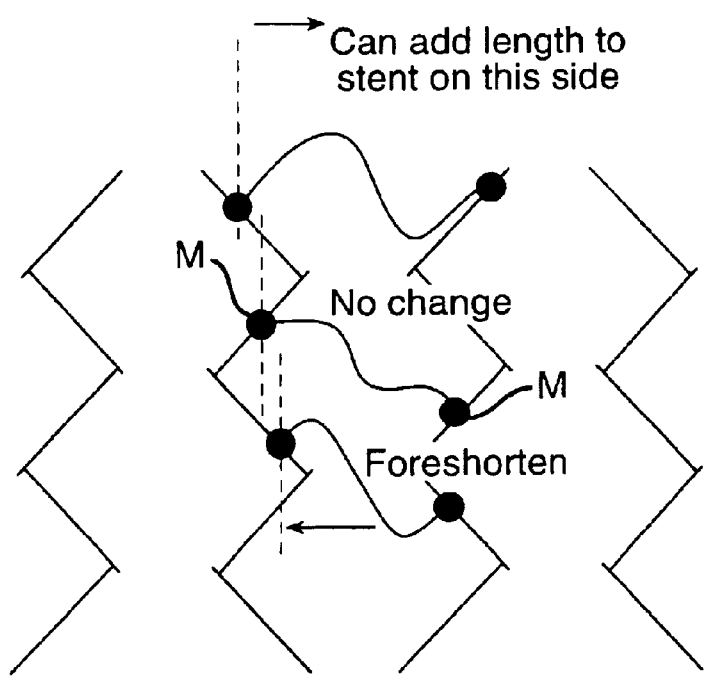

As can be seen from FIGS. 8, 9 and 10, there is provided yet another embodiment of the stent 400 in the present invention. Again, the stent 400 provides for generally stronger radial sections R comprising radial struts 410, which are generally slotted in alternating fashion around the circumference of the stent. The flexible connector members 420 are similar to the flexible connector members as seen in FIG. 7, and also to the flexible connector members of the Bx Velocity® stent. However, these flexible connector members 420 are connected to the radial struts generally somewhere near the midpoint of the radial struts 410. In this fashion, upon expansion the length of the connector members 420 remains independent of the shortening or lengthening of the radial struts 410. In this way, the overall length of the stent is maintained, as seen from the schematics in FIGS. 9 and 10.

Due to this overall ability to maintain the length of stent 400, the radial struts 410 provide for radial strength only, and do not contribute in one way or another to any foreshortening of the stent. Also, the radial struts 410 are formed from a generally "wavy" pattern. This wavy pattern is useful in helping to reduce the crimp profile of the stent 400 on the balloon. This results from the relative smooth attachment of the radial struts 410 to the flexible connectors 420. Further, having such an arrangement reduces the strain placed on the struts 420 upon expansion. This reduced strain is achieved due to the location of the connection of the struts 420 to the struts 410. Because there is relatively little movement of the struts 420 in the longitudinal direction, there is relatively little strain placed on these struts during expansion. The radial arcs 415 of struts 410 can be ideally placed in a "shifted" configuration so that the stent is easier to crimp on a balloon.

Further, this can be seen from FIG. 8, that the radial strut members 410 are attached to the flexible connectors 420 so that the flexible connectors 420 generally proceed along a "spiral" pattern S around the length of the stent 400. The connection points 422 of the flexible connectors 420 are placed in a diagonal fashion on struts 410 so as to enhance flexibility. Generally connectors 422 are located on a midpoint of a strut 410. When the connectors 422 are placed past the midpoint of strut 410 (i.e., farther from the midpoint of strut 410 than from the direction of connector 420), the nominal stent strength should increase upon expansion when compared to the above described stent. This arrangement reduces foreshortening, as described above. Further, the arrangement in no wise affects any torsion on the stent as it is applied to the lumen by the balloon catheter. Friction of the balloon to struts 410 maintains the struts 410 (and their opposite struts 420) in the same general radial position throughout expansion. By reducing any concern of stent torsion, there is also a reduced concern of overall slippage of the balloon. Even though the connector members 420 are not aligned with one another, they are maintained in their respective positions on the balloon surface. Upon expansion, struts 420 lock into place, as the stent 400 is placed, giving an increased strength in the lumen.

From FIGS. 8 and 9, we see that the midpoint of a connector 420 is important to maintaining length. The greater the distance from connector 420 to the midpoint M, on the side of the connection between struts 410, 420, the greater the potential for shortening of the stent. This creates a need to solve any shortening by other means, absent the solution described herein.

It is to be understood that various modifications to the stent 400 of FIGS. 8, 9 and 10 are possible without departure from the invention herein. For instance, the connectors 420 can be placed intermittently about the stent 400 circumference, and not at every incidence of a radial strut 410. Also, while the radial struts 410 are generally 90° out of phase between one series of struts 410a and the next 410b, it is foreseeable to place them between 30° to 150° out of place. When so placed, the struts 410 can be "encouraged" to bend in a particular fashion, which may be preferential in the design of a particularly intended stent.

These stents can be manufactured by know conventional means, such as laser etching, electrical discharge machining (EDM), photochemical etching, etc. However, there is also disclosed in the invention herein a novel method of performing photochemical resistance etching of the tube from which the stent is to be made. This novel method allows one to produce a stent with variable geometry in the three dimensions of the strut, that is, along its length, across the circumferential dimension, and along its depth (or radial dimension.) This method starts with a standard photochemical machining process.

The new process consists of cutting the stent using photochemical etching, cleaning it, and then coating it with a photoresist. The photoresist coating is applied in circular shapes 290, as can be appreciated from FIG. 6. These shapes 290 are intentionally figured to be of varying dimension in their radius. Then, a photoresist image is developed on the surface of the cylindrical metallic tube T from which the stent starts. This photoresist image is developed in a controlled fashion using known means. The development of the photoresist in this fashion allows a controlled variable etching rate at select positions along the cylindrical metallic tube.

Figure 6:
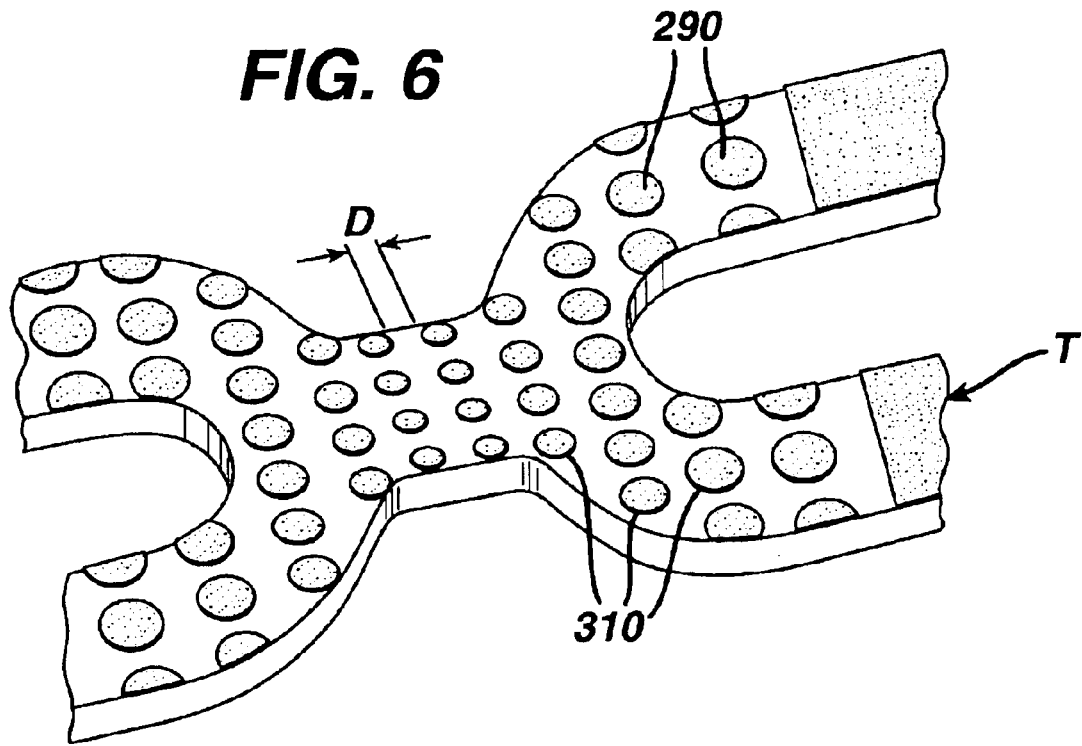
FIG. 6 is a schematic of a photoresist pattern formed on the stent in order to perform a method for making the stent as described in the invention.

As previously stated, the novel photoresist image can be seen in FIG. 6. This photoresist image consists of a series of circular regions of photoresist material 310, which are shaped in a variable diameter as desired for manufacture. These photoresist images 310 are configured at variable distances D from one another. As the diameter of the circular photoresist pattern 310 decreases, and its distance from other photoresist patterns 310 increases, the etching rate of that area of the stent increases. Thus, by strategically placing the photoresist patterns 310 on the stent, one can produce any variable dimension in any direction along the stent.

This photoresist pattern 310 variation results in a variation in the metal of the stent removed during the etching process. This process can be used to locally change the geometry of the metallic tube.

In this fashion, one can envision making a stent of variable circumferential width, radial depth or longitudinal length. As such, one can impart varying flexibilities along the stent longitude, as well as varying strengths so that a stent can be configured for emplacement at various locations within the body.

What is claimed is:

1. A stent having a generally tubular shape and a longitudinal axis, comprising:

a plurality of columnar sections and a plurality of flexible sections, each of said sections arranged circumferentially around said generally tubular shape, and a said columnar section attached to at least one flexible section, and said columnar section and flexible section each having predetermined longitudinal lengths, and wherein said columnar sections and said flexible sections each maintain their respective longitudinal lengths during expansion of the stent from a first unexpanded configuration to a second expanded configuration.

2. The stent of claim 1 wherein consecutive flexible sections are out of phase with one another.

3. The stent of claim 1 wherein the flexible sections have an axis that is non-parallel to the longitudinal axis of the stent.

4. The stent of claim 3 wherein consecutive flexible sections are out of phase with one another.

5. The stent of claim 3 wherein the flexible sections are connected to columnar sections by means of connector members, said connector members placed out of phase with one another.

6. The stent of claim 1 wherein the flexible sections have an axis parallel to the longitudinal axis of the stent.

7. The stent of claim 6 wherein consecutive flexible sections are out of phase with one another.

8. The stent of claim 6 wherein the flexible sections are connected to columnar sections by connector members, said connector members placed out of phase with one another.

9. The stent of claim 1 wherein the flexible sections are connected to columnar sections by connector members, said connector members placed out of phase with one another.

* * * * *